US006459764B1

(12) United States Patent
Chalmers et al.

(10) Patent No.: US 6,459,764 B1
(45) Date of Patent: Oct. 1, 2002

(54) DRIVE-THROUGH VEHICLE INSPECTION SYSTEM

(75) Inventors: Alexander Chalmers, Norwood; Peter Rothschild, Newton; Lee Grodzins, Lexington, all of MA (US)

(73) Assignee: American Science and Engineering, Inc., Billerica, MA (US)

( * ) Notice: Subject to any disclaimer, the term of this patent is extended or adjusted under 35 U.S.C. 154(b) by 1 day.

(21) Appl. No.: 09/631,140

(22) Filed: Aug. 2, 2000

Related U.S. Application Data

(63) Continuation-in-part of application No. 09/238,686, filed on Jan. 27, 1999, now Pat. No. 6,151,381.

(51) Int. Cl.⁷ .......................................... G01N 23/203
(52) U.S. Cl. ........................................ 378/88; 378/86
(58) Field of Search .......................... 378/57, 86, 87, 378/88, 89, 90

(56) References Cited

U.S. PATENT DOCUMENTS

| | | | |
|---|---|---|---|
| 4,799,247 A | 1/1989 | Annis et al. ................... 378/87 |
| 5,065,418 A | 11/1991 | Bermbach et al. ............. 378/57 |
| 5,600,700 A | 2/1997 | Krug et al. .................... 378/57 |
| 5,638,420 A | * 6/1997 | Armistead .................... 378/146 |
| 5,642,393 A | 6/1997 | Krug et al. .................... 378/57 |
| 5,764,683 A | * 6/1998 | Swift et al. .................... 378/57 |
| 5,910,973 A | 6/1999 | Grodzins ....................... 378/57 |
| 5,917,880 A | 6/1999 | Bjorkholm .................... 378/57 |
| 6,192,104 B1 | * 2/2001 | Adams et al. ................. 378/90 |
| 6,249,567 B1 | * 6/2001 | Rothschild et al. ........... 378/88 |
| 6,282,260 B1 | 8/2001 | Grodzins ....................... 378/87 |

FOREIGN PATENT DOCUMENTS

GB 2 277 013 2/1994 .......... G01N/23/04

OTHER PUBLICATIONS

Application No.: 09/599,386, Jun. 6, 2000.

* cited by examiner

Primary Examiner—David P. Porta
(74) Attorney, Agent, or Firm—Bromberg & Sunstein LLP

(57) ABSTRACT

An inspection system for inspecting a moving vehicle and for detecting material disposed within the vehicle. The system has a source for providing a generally horizontally pointing beam of penetrating radiation of specified cross-section so as to illuminate vehicles driven alongside the source of radiation. A detector arrangement, disposed between the source of radiation and the moving vehicle detects radiation from the beam scattered by any material disposed on the underside of the moving vehicle and generates a scattered radiation signal that may be used for characterizing the material disposed within the vehicle.

20 Claims, 2 Drawing Sheets

DRIVE-THROUGH VEHICLE INSPECTION SYSTEM

This application is a continuation-in-part of U.S. patent application Ser. No. 09/238,686, filed Jan. 27, 1999 and now issued as U.S. Pat. No. 6,151,381, and contains subject matter related to that of U.S. application Ser. No. 09/395,331, filed Sep. 13, 1999, now issued as U.S. Pat. No. 6,249,567, all of which applications and patents are herein incorporated by reference.

TECHNICAL FIELD

The present invention relates to a system and method for detecting materials concealed within, or on, a vehicle, particularly for inspecting a vehicle when personnel are present within, and driving, the vehicle.

BACKGROUND OF THE INVENTION

It is desirable to determine the presence of objects, such as contraband, weapons, or explosives, that have been concealed, for example, in a moving vehicle, or, additionally, under the moving vehicle, in either case, without requiring the subjective determination of a trained operator. The determination should be capable of being made while the container is in motion, indeed, as inspection rate and thus hourly throughput is at a premium, it is desirable that the vehicle be driven without requiring the driver or passengers to alight. In case a detection is made, a visual image should be available for verification.

The use of images produced by detection and analysis of penetrating radiation scattered from an irradiated object, container, or vehicle is the subject, for example, of U.S. Pat. No. 4,799,247 (Annis et al.) and U.S. Pat. No. 5,764,683 (Swift et al.), where are herein incorporated by reference. The techniques taught in these patents require that the motion of the inspected object relative to the source of radiation be at a controlled rate, either by moving the inspected object on a conveyor, by sweeping the orientation of the source, or by mounting both source and detector arrangement on a single movable bed and driving them past the inspected object at a known or determinable rate.

UK Patent (issued from Application 2 277 013, filed Mar. 31, 1994) to Bermbach teaches the examination of a loaded truck by driving it through an examination bay while irradiating one side with a fan beam of low-energy x-rays while detecting the x-rays transmitted through the truck with detectors formed from an angular strip. The detectors are taught to be formed from a series of detector elements such that their output signals may be converted into an image of the relevant irradiated zone of the truck.

U.S. Pat. No. 5,917,880, to Bjorkholm, issued Jun. 29, 1999, teaches moving a vehicle on a conveyor at a regulated speed through a bay in which it is illuminated by a fan beam of high-energy x-rays in the range of 1–8 MeV, the high energy being required so that the x-rays fully traverse the vehicle and its cargo for detection, on the opposite side of the vehicle, of forward scattered radiation.

Another system for using x-rays transmitted through a moving vehicle, such as a moving railway car or other large shipping container, has been taught in U.S. Pat. No. 5,910,973, to Grodzins, issued Jun. 8, 1999, and incorporated herein by reference. Grodzins taught embodiments wherein transmitted x-rays are detected by one or more detectors placed on the side of the car distal to the source of irradiation. Disadvantages of the inspection systems based on transmitted x-rays include their typical insensitivity to organic materials having low attenuation, especially those in sheet form, and, especially, the requirement that sufficiently energetic x-rays be used to penetrate the entire thickness of the inspected vehicle. This makes a transmission-based inspection system inappropriate for the inspection of automobiles, and may also limit other applications due to the implicit safety threat to humans who are either known to be in the vehicles or else concealed there.

SUMMARY OF THE INVENTION

In accordance with one aspect of the invention, in one of its embodiments, there is provided an inspection system for inspecting a moving vehicle. The system has a source of radiation for providing a beam of penetrating radiation of specified cross-section directed in a beam direction substantially horizontal and transverse to the direction of motion of the vehicle. Furthermore, the system has a detector arrangement disposed between the source of radiation and the moving vehicle for detecting radiation from the beam scattered by any material disposed within the moving vehicle and for generating a scattered radiation signal, and a controller for characterizing the material disposed within the moving vehicle based at least on the scattered radiation signal.

In accordance with various embodiments of the invention, the inspected vehicle may be a train car, an automobile, or a truck. The source of penetrating radiation may be an x-ray source, and the source of penetrating radiation may include a beam scanning mechanism such as a rotating chopper wheel or an electromagnetic scanner. The beam itself may be shaped as a pencil beam.

Alternate embodiments of the invention may additionally have a second source for providing a second beam of penetrating radiation of specified cross-section directed in a second beam direction transverse to the direction of motion of the vehicle and a second detector arrangement disposed between the second source of radiation and the moving vehicle. The inspection system may also have a display for displaying a scatter image of the material disposed in the interior of the vehicle and a processor for associating pre-stored characteristics of the vehicle such that the scattered radiation signal may be compared with the pre-stored characteristics. Additionally, the inspection system may have a velocity sensor for registering the velocity of the vehicle with respect to the inspection system.

In accordance with yet further embodiments of the invention, the beam of penetrating radiation may have a variable energy spectrum and the controller may characterize the material disposed inside the vehicle based at least on combination of the scattered radiation signal under conditions of illumination with a first energy spectrum and the scattered radiation signal under conditions of illumination with a second energy spectrum.

BRIEF DESCRIPTION OF THE DRAWINGS

The foregoing features of the invention will be more readily understood by reference to the following detailed description taken with the accompanying drawings.

DETAILED DESCRIPTION OF PREFERRED EMBODIMENTS

Methods and advantages of backscatter inspection of a moving vehicle by illuminating the vehicles with x-rays from either above or beneath the moving vehicle are described in co-pending U.S. application Ser. No. 09/395,331, filed Sep. 13, 1999, and now issued as U.S. Pat. No. 6,249,567. In accordance with preferred embodiments of the present invention, regions of enhanced backscatter that arise due to materials concealed close to the side walls of a vehicle are revealed without requiring that penetrating radiation traverse the vehicle during the course of inspection.

Figure 1:
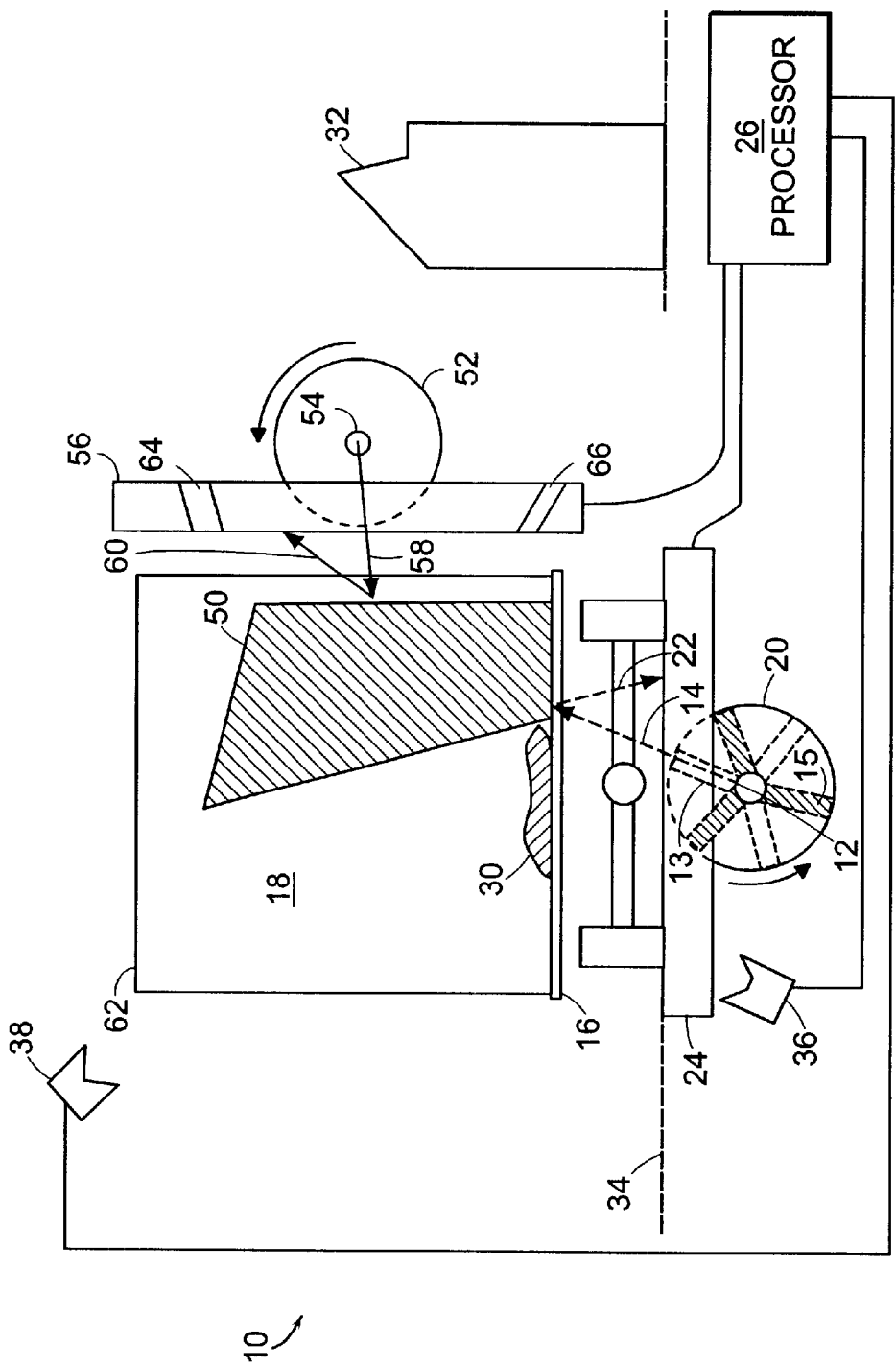
FIG. 1 provides a rear view in cross-section of an inspection system employing a beam for irradiating a moving vehicle from the side and a detection arrangement for inspection of the vehicle in accordance with a preferred embodiment of the present invention.

FIG. 1 shows a rear view in cross-section of the elements of an inspection system, designated generally by numeral 10. A source 54 emits penetrating radiation in a beam 58 having a cross-section of a specified shape. Beam 58 of penetrating radiation, may be, for example, a beam of x-rays such as a polychromatic x-ray beam. Source 54 of penetrating radiation is preferably an x-ray tube, for example, however other sources of penetrating radiation, such as a LINAC (linear accelerator), are within the scope of the present invention. The energy range of the penetrating radiation emitted by source 54 is discussed further below.

Figure 2:
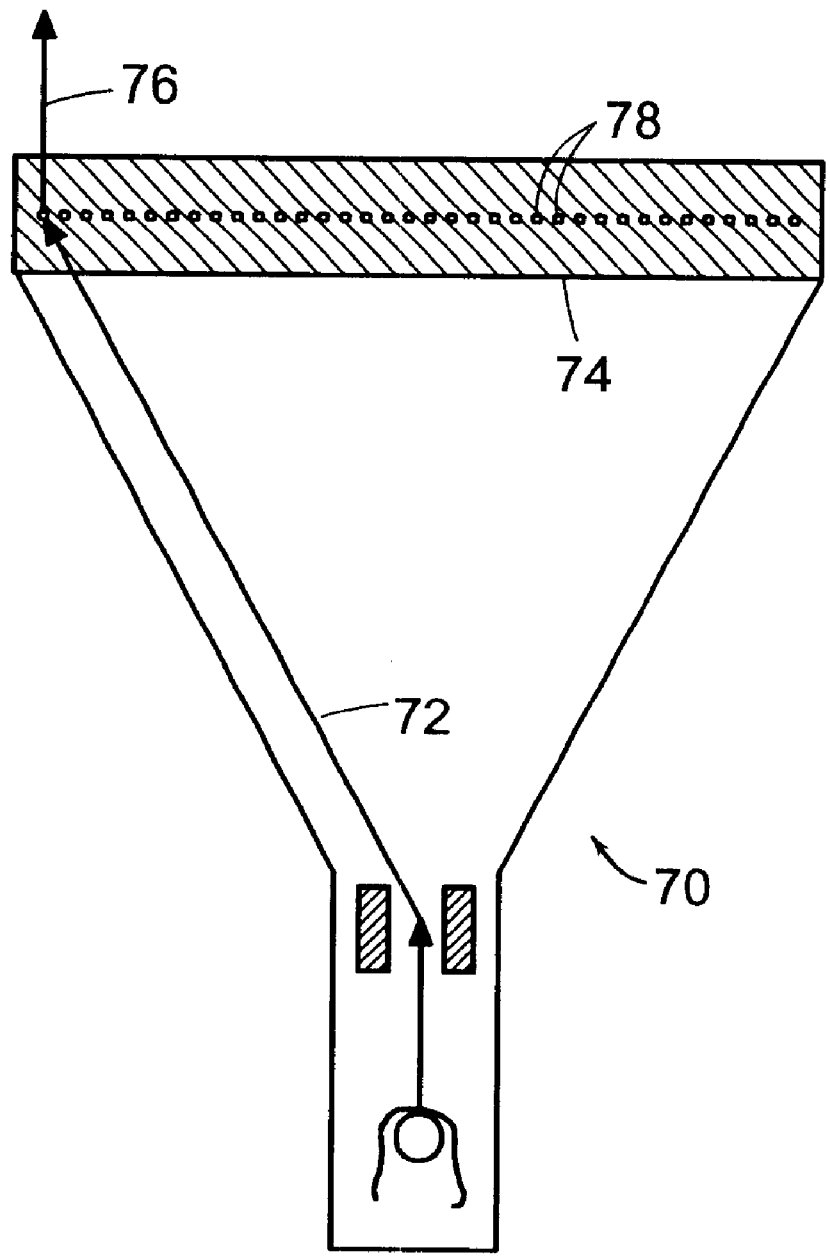
FIG. 2 shows a schematic representation, in plan view, of an electromagnetically scanned source of x-ray beams.

A scanning mechanism 52 is provided for scanning beam 58 along a substantially vertical axis, as a vehicle 18 or other object that is to be inspected moves past beam 58 in a substantially horizontal direction, into the page, in the depiction of FIG. 1. Scanning mechanism 52 may be a flying spot rotating chopper wheel as known to persons skilled in the art. Alternatively, electromagnetic scanners 70 may be employed, as shown in FIG. 2 and described in detail in co-pending U.S. patent application, Ser. No. 09/599,386, filed Jun. 22, 2000 and now allowed, entitled "Method And Apparatus For Generating Sequential Beams of Penetrating Radiation," which is incorporated herein by reference. In accordance with one embodiment, an electromagnetic scanner includes a charged particle beam 72 that may be accelerated towards, and electromagnetically scanned across, a target 74, thereby generating x-rays 76 that emanate from a succession of points on the target. The emitted x-rays may pass through one or more collimator apertures 78, thereby creating a sequence of beams having distinct orientations. Various embodiments of an electromagnetic scanner are described in co-pending U.S. patent application, Ser. No. 09/599,386.

Inspected vehicle or container 18 may be self-propelled through beam 58 or may be pulled by a mechanized conveyor or tractor. Container 18 is typically a truck, and is depicted as such in FIG. 1, where trailer 18 is shown being pulled in a direction into the page.

Beam 58 will be referred to in the present description, without limitation, as an x-ray beam. In accordance with a preferred embodiment of the invention, rotating chopper wheel 52 is used to develop a pencil beam 58 which may be swept in a plane substantially parallel to that of the page. The formation of a pencil beam 14 is shown in greater detail with respect to a supplementary scanning mechanism 20 disposed beneath vehicle 18 in accordance with an alternate embodiment of the invention, however pencil beam 58 may be formed in a similar manner. A series of tubular collimators 13 distributed as spokes on rotating wheel 20 is known in the art. The cross section of pencil beam 14 is of comparable extent in each dimension and is typically substantially rectangular, although it may be many shapes. The dimensions of pencil beam 14 typically define the scatter image resolution which may be obtained with the system. Other shapes of beam cross section may be advantageously employed in particular applications.

A detector arrangement 56 is disposed in a plane disposed parallel to the direction of locomotion of vehicle 18. X-rays 60 scattered by Compton scattering out of beam 58 in an essentially backward direction are detected by one or more backscatter detectors 56 disposed between source 54 and vehicle 18. A similar detector arrangement 24 may be used supplementarily for detecting x-rays 22 Compton-scattered from beam 14 which may be disposed below vehicle 18, or, alternately, may be disposed on the side of vehicle 18 opposing beam 58.

Within the scope of the invention, any x-ray detection technology known in the art may be employed for backscatter detector arrangement 56. The detectors may be scintillation materials, either solid or liquid or gaseous, viewed by photo-sensitive detectors such as photomultipliers or solid state detectors. Liquid scintillators may be doped with tin or other metal. Respective output signals from the scatter detectors 56 are transmitted to a processor 26, and processed to obtain images of object 30 inside the vehicle.

Other characteristics may be obtained using backscatter techniques, such, for example, as mass, mass density, mass distribution, mean atomic number, or likelihood of containing targeted threat material, all as known to persons skilled in the art of x-ray inspection.

In accordance with preferred embodiments of the invention, x-rays having maximal energies in the range between 160 keV and 300 keV are employed. At this energy, x-rays penetrate into the vehicle, and organic objects inside the vehicle can be detected. Since lower doses of x-ray irradiation are thus possible, automobiles may be scanned using the present invention. For applications where the scanned vehicle may contain personnel, end point energies below 220 keV are preferred.

Various methods known in the art may be employed for determining the location in three dimensions of the contents 50 of container 18. For example, the use of detector elements 64 and 66 asymmetrically disposed with respect to source 54 may be used to determine the depth of scattering material in accordance with an algorithm described in co-pending U.S. patent application, Ser. No. 09/458,479, filed Dec. 9, 1999, which is incorporated herein by reference.

As vehicle 18 passes the inspection point, an inspection is performed, resulting either in the triggering of an alarm, under specified conditions, or a two-dimensional scatter image may be displayed to an operator, at console 32. Additionally, an alarm may be triggered and an image displayed. The motion of vehicle 18 may be monitored by known sensor means to provide a scaling of the axis of the image along the direction of motion. In particular, a measure of the instantaneous speed may be obtained by means of any sort of velocity sensor 38 such as a microwave Doppler sensor, for example. Knowledge of the instantaneous speed of the vehicle allows undistorted images of the cargo and undercarriage of the vehicle to be obtained by adjusting pixel width and position (registration) according to vehicle speed, as known to persons skilled in imaging.

In accordance with alternate embodiments of the invention, automatic algorithms may be used to detect regions of enhanced backscatter in the image or regions meeting other specified criteria with respect to size, shape or composition. When such a region is detected, the operator is alerted, and the suspicious area is high-lighted for the operator on the backscatter image. For checkpoints into controlled facilities, in accordance with a further embodiment, a sensor, such as a bar-code reader, enables the backscatter image to be compared by a processor with pre-stored features of the vehicle undergoing inspection which may correspond to a spatial regularity of highly scattering members, for example.

In accordance with a further embodiment of the invention, a dual-energy technique is employed for obtaining two views (or a combined view) of the vehicle contents in order to detect organic contraband automatically. A dual-energy backscatter technique is especially useful when the end point energy of the x-ray beam may exceed about 80 keV. Referring again to FIG. 1, a 160 kV x-ray source 54 with a tungsten anode may be employed, for example, with a beam-forming chopper wheel with six spokes 13. An energy-selective x-ray absorber 15 is placed in alternate arms so as to absorb out the lower-energy components of the x-ray spectrum thereby producing an x-ray beam having a spectrum in which most of the intensity of the beam is at energies greater than about 80 keV. The backscatter view taken with the absorber-filled spokes is thus produced by the high-energy radiation in the x-ray beam.

A view taken with the energetic beam (through an absorber-filled spoke) may be combined, in accordance with embodiments of the invention, with a view taken with a beam containing a more substantial fraction of low-energy photons. Combination may be performed using one or more of a variety of algorithms known in the art for combining scatter images. For example, the ratio of the intensities of corresponding pixels may be taken, thereby providing a higher level of confidence in a determination of atomic number than may be obtained in either view taken alone. The high-energy view is dominated by Compton scattering, which is substantially independent of the scattering material. The low-energy view may be dominated by the photoelectric effect, which is strongly material-dependent. The ratio of the two views thus provides a measure of the material qualities substantially independent of geometrical effects and changes in signal output having their origin in temperature of component variability. Thus, source-object and detector-object variations may be normalized out, using algorithms known in the art. Additionally, data or images obtained from detected scattered radiation may be combined with optical images, obtained with a video camera 36 (shown in FIG. 1), for example, so that images of suspected contraband, obtained with modest spatial resolution, may be superposed on a high-resolution optical image for evaluation by an operator.

The use of backscatter detection may advantageously provide for detection of threat items located within the vehicle enclosure close to the side wall of the vehicle irradiated by beam 58 without requiring x-rays of such high energy as to traverse the enclosure entirely and to be detected at the far side of the vehicle. The use of lower energy x-rays is preferred for reasons of personnel safety and shielding requirements.

The described embodiments of the invention are intended to be merely exemplary and numerous variations and modifications will be apparent to those skilled in the art. All such variations and modifications are intended to be within the scope of the present invention as defined in the appended claims.

We claim:

1. An inspection system for inspecting a vehicle moving in a direction, the system comprising:
    a. a source for providing a beam of penetrating radiation of specified cross-section directed in a beam direction substantially horizontal and transverse to the direction of motion of the vehicle;
    b. a detector arrangement disposed between the source of radiation and the moving vehicle for detecting radiation from the beam scattered by any material disposed within the moving vehicle and for generating a scattered radiation signal;
    c. a controller for characterizing the material disposed within the moving vehicle based at least on combination of the scattered radiation signal under conditions of illumination with a first energy spectrum and the scattered radiation signal under conditions of illumination with a second energy spectrum.

2. The inspection system as set forth in claim 1, wherein the vehicle is chosen from the group of a train car, an automobile, and a truck.

3. The inspection system as set forth in claim 1, wherein the source of penetrating radiation is an x-ray source.

4. The inspection system as set forth in claim 1, wherein the source of penetrating radiation includes a beam scanning mechanism.

5. The inspection system as set forth in claim 4, wherein the beam scanning mechanism is a rotating chopper wheel.

6. The inspection system as set forth in claim 4, wherein the beam scanning mechanism is an electromagnetic scanner.

7. The inspection system as set forth in claim 1, wherein the beam of penetrating radiation is a pencil beam.

8. The inspection system as set forth in claim 1, further comprising:
    a. a second source for providing a second beam of penetrating radiation of specified cross-section directed in a second beam direction transverse to the direction of motion of the vehicle; and
    b. a second detector arrangement disposed between the second source of radiation and the moving vehicle for detecting radiation from the second beam scattered by any material disposed within the moving vehicle and for generating a second scattered radiation signal.

9. The inspection system as set forth in claim 1, further including a display for displaying a scatter image of the material disposed in the interior of the vehicle.

10. The inspection system as set forth in claim 1, further including a display for displaying a scatter image of the material disposed on an undercarriage of the vehicle.

11. The inspection system as set forth in claim 1, further including a processor for associating pre-stored characteristics of the vehicle such that the scattered radiation signal may be compared with the pre-stored characteristics.

12. The inspection system as set forth in claim 1, wherein the source of penetrating radiation emits x-rays with an end-point energy between 50 and 500 keV.

13. The inspection system as set forth in claim 1, wherein the source of penetrating radiation emits x-rays with an end-point energy below 220 keV.

14. The inspection system as set forth in claim 1, further comprising a velocity sensor for registering the velocity of the vehicle with respect to the inspection system.

15. The inspection system as set forth in claim 1, wherein the beam of penetrating radiation has a variable energy spectrum.

16. An inspection system for inspecting a vehicle moving in a direction, the system comprising:
    a. a source for providing a beam of penetrating radiation of specified cross-section directed in a beam direction substantially horizontal and transverse to the direction of motion of the vehicle;

b. a detector arrangement including at least two detectors disposed asymmetrically with respect to the source, disposed between the source of radiation and the moving vehicle for detecting radiation from the beam scattered by any material disposed within the moving vehicle and for generating a scattered radiation signal; and c. a controller for characterizing the material disposed within the moving vehicle based at least on the scattered radiation signal.

17. A method for inspecting contents of a moving vehicle, the method comprising:

a. illuminating the vehicle with penetrating radiation formed into a substantially horizontal beam, the penetrating radiation first having a first spectral composition and then illuminating the moving vehicle with penetrating radiation having a second spectral composition;

b. detecting radiation from the beam scattered by any material disposed within the moving vehicle to generate a scattered radiation signal; and c. characterizing the material disposed within the moving vehicle based at least on the scattered radiation signal.

18. A method according to claim 17, wherein the step of characterizing the material disposed within the vehicle includes combining the scatter radiation signal obtained during illumination with the first spectral composition with the scatter radiation signal obtained during illumination with the second spectral composition.

19. A method according to claim 17, further including:

d. varying the orientation of the beam with respect to the vehicle.

20. A method according to claim 17, further including:

d. displaying a scatter image of the scattered radiation signal.

* * * * *